[19] United States Patent
Debras et al.

[11] Patent Number: 4,861,939
[45] Date of Patent: Aug. 29, 1989

[54] PROCESS FOR REMOVING ARSINE FROM LIGHT OLEFIN CONTAINING HYDROCARBON FEEDSTOCKS

[75] Inventors: Guy Debras, Les-Bons-Villers; Philippe Bodart, Mozet, both of Belgium

[73] Assignee: Labofina, S.A., Brussels, Belgium

[21] Appl. No.: 248,533

[22] Filed: Sep. 23, 1988

[30] Foreign Application Priority Data

Sep. 24, 1987 [EP] European Pat. Off. ........ 87870137.4

[51] Int. Cl.⁴ ............................................. C10G 17/02
[52] U.S. Cl. .................... 585/820; 208/253; 208/251 R; 208/299; 208/310 R; 55/74; 423/87; 423/210; 585/823; 585/850; 585/855
[58] Field of Search ................. 208/253, 251 R, 299, 208/244, 310 R; 55/74; 585/820, 850, 855; 423/87, 210 M

[56] References Cited

U.S. PATENT DOCUMENTS

| 2,951,034 | 8/1960 | Stuart | 585/850 |
| 3,782,076 | 1/1974 | Carr et al. | 55/74 |
| 3,833,498 | 9/1974 | Stahfeld | 208/307 |
| 3,933,624 | 1/1976 | Myers | 208/253 |
| 4,069,140 | 1/1978 | Wunderlich | 208/253 |
| 4,075,085 | 2/1978 | Young | 208/253 |
| 4,083,924 | 4/1978 | Styring | 208/253 |
| 4,439,313 | 3/1984 | Schindler et al. | 423/87 |
| 4,535,072 | 8/1985 | Kitayama et al. | 55/74 |
| 4,605,812 | 8/1986 | Nowack et al. | 208/253 |

Primary Examiner—H. M. S. Sneed
Assistant Examiner—Helane Myers
Attorney, Agent, or Firm—William D. Jackson; John K. Abokhair; M. Norwood Cheairs

[57] ABSTRACT

The present invention relates to a process for removing arsine from a light olefin to containing hydrocarbon feedstock, said process comprising the steps of (a) passing said feedstock over an absorbent material comprising nickel deposited on a support material wherein nickel is present as both nickel oxide and metallic nickel; and (b) recovering a stream having a substantially reduced arsine content.

25 Claims, No Drawings

PROCESS FOR REMOVING ARSINE FROM LIGHT OLEFIN CONTAINING HYDROCARBON FEEDSTOCKS

FIELD OF THE INVENTION

The present invention relates to a process for removing arsenic, present in the form of arsenic hydride or arsine, from light olefin-containing hydrocarbons. More particularly, the present invention relates to a process for the removal of arsine from hydrocarbon feedstocks containing propylene.

BACKGROUND OF THE INVENTION

Industrial applications of light olefin-containing hydrocarbons, and particularly liquified propylene, have become more increasingly specialized. The technology as presently developed utilizes highly efficient catalysts to convert these hydrocarbon feedstocks into final product such as polymers. However, these highly efficient catalysts are very sensitive to contaminants, particularly arsenic contaminants, found in these hydrocarbon feedstocks.

In addition to the well known contaminants such as hydrogen sulfide and mercaptans, the light olefin-containing hydrocarbon feedstocks normally contain a small quantity of arsine. Usually arsine is present to the extent of only several hundred parts per million (ppm) by weight. However, even this small amount is normally beyond the allowable limits of an acceptable product.

The presence of arsine, even at very low concentrations, oftentimes renders olefins valueless for many purposes. For example, high purity olefins are required for the satisfactory production of many polymeric products, especially those useful as plastics, including polymers of ethylene, propylene, and the like. However, arsine is a powerful reducing agent which appears able to reduce the olefin polymerization catalysts and cause their deactivation. As a result, there has been a real need to improve techniques for removing arsine from light olefin-containing hydrocarbons, especially those used for polymer production.

Some of the known methods for removing arsine from light olefin containing hydrocarbon streams include the following.

U.S. Pat. No. 3,782,076 (Carr et al., assigned to GULF R & D) discloses a process for reducing the arsenic content, believed to be present as arsine, from gaseous hydrocarbon streams by contacting said streams with supported lead oxide; however, the presence of sulfur compounds is said to interfere with the removal of arsine, and further the supported lead oxide may not be regenerated when sulfur compounds are present in the feed.

U.S. Pat. No. 3,833,498 (Stahfeld, assigned to GULF R & D) discloses a process for reducing the arsenic content, believed to be present as arsine, from gaseous hydrocarbon streams by contacting said streams with activated carbon derived from a bituminous coal and containing cobalt, nickel, molybdenum and vanadium. However, the feed should be substantially dry and free of sulfur compounds.

The purification of propylene and the like olefin feed streams is particularly complicated by the small difference between the boiling points of propylene and arsine which hampers arsine removal by fractionation. Consequently, the levels of arsine impurity in propylene stocks are oftentimes intolerably high.

Accordingly, it can be seen that there is a need for a process to reduce the arsine concentration in a light olefin-containing hydrocarbon stream to 50 ppb by weight or lower.

SUMMARY OF THE INVENTION

The present invention is directed to a process for the removal of arsine from light olefin-containing hydrocarbon feedstocks, and more particularly from hydrocarbon feedstocks containing propylene and from about 0.06 to 150 ppm by weight of arsine. In accordance with the present invention, arsine is removed by passing the hydrocarbon feed over an absorbent material comprising nickel deposited on a support material and wherein the nickel is present in the forms of metallic nickel and nickel oxide. The total weight of nickel and nickel oxide can range up to about 80% by weight of the absorbent, with the provision that metallic nickel content is within the range of 10 wt. %–50 wt. % of the absorbent.

DETAILED DESCRIPTION

The present invention relates to the removal of arsenic hydride, often referred to as arsine, from light olefin-containing hydrocarbon streams. Light olefins, as used herein, are $C_2$–$C_6$ olefins. Of particular interest is the treatment of hydrocarbon streams containing light olefins which are to be subsequently subjected to polymerization using polymerization catalysts. As stated previously, hydrocarbon streams containing propylene present a special problem because of the closely related boiling points of propylene and arsine. While the subsequent discussion will describe the invention in terms of treating propylene-containing feeds, it should be understood that the present invention is applicable to the treatment of light olefin-containing hydrocarbon streams in general, i.e., hydrocarbon streams containing ethylene, propylene, butenes, pentenes, hexenes, or any combination thereof.

In addition to arsine, another possible contaminant of hydrocarbon is stibine ($5bH_3$). Stibine is less stable than arsine and is not formed readily. However, based upon the experimental data set forth below, it is believed that, in addition to arsine, the present invention will also result in the removal of stibine from feedstocks of the type described herein.

The arsine removal process of the present invention reduces the arsine concentration in the treated hydrocarbon feedstock to 50 parts per billion by weight (ppb) or lower. The original arsine concentration may be as high as 1000 parts per million by weight (ppm) or higher depending on the process of making and the origin of the hydrocarbon feedstock. Due to the expense and specialization of the present invention, it is preferred to utilize other less costly and less complex processes to reduce the arsine concentration to 70 ppm or less prior to treatment in accordance with the present invention.

The absorbent material used in the present invention comprises nickel deposited on a support material, the nickel being present both as metallic nickel and as nickel oxide. Silica, silica-aluminas, alumina, kieselguhr, zeolites and other similar materials, whether amorphous or crystalline, can be utilized as the support. The total weight of nickel and nickel oxide may represent up to about 80 wt. % of the absorbent material, with the provision that metallic nickel should not represent less than 10 wt. % nor more than 50 wt. % of the absorbent. The absorbent includes 20 wt. % or more of the support material. Preferably, the weight ratio of metallic nickel to nickel oxide is of about 0.4 to about 2.0, and the absorbent comprises from about 30 to about 60 wt. % of support material. When carrying out the process of the invention with an absorbent material outside this definition, the results obtained are less satisfactory, although some arsine may still be removed. While the invention is not to be limited by any theory, it is believed that larger crystallites are formed if the Ni/NiO ratio is higher than 2.0, thus leading to a lesser efficiency; similarly, an excessive total nickel content tends to lower the specific surface and consequently the efficiency, while a too low total nickel content would lead to an insufficient capacity for absorbing arsine.

The nickel can be deposited on the support by any suitable technique. Several methods well known to those skilled in the art. For example, nickel can be deposited on the support by dissolving nickel nitrate in water, mixing the solution with the support and precipitating the nickel, for example in the form of nickel carbonate, and subsequently washing, drying and calcining the precipitate. The nickel deposited in this manner is then partially reduced by means of hydrogen to form metallic nickel, the remainder being in the form of nickel oxide.

In general, the size of the nickel crystallites after reduction is from about 1 to about 20 nanometers nm). A more specific size range is about 1-2 nanometers. The size of the nickel crystallites depends on the extent of reduction carried out. In fact, if the degree of reduction is increased excessively, the size of the crystallites is increased to above the aforementioned range but the absorbent material obtained does not have the preferred properties. On the other hand, if the degree of reduction is too low, the crystallites still have good dimensions but the quantity of nickel available in this case is too small to ensure successful purification of the feedstock.

The specific surface area of the absorbent material obtained after reduction is generally between 100 and 200 m$^2$/g.

The particle size of the absorbent material depends especially on the pressure drop allowed in the reactor; it has been noted, however, that it is advantageous to use the absorbent material in finely divided form. Preferably, the particle diameter of this material when spherical does not exceed about 3.5 mm and is most preferably from about 1 to about 2.5 mm; when cylindrical particles are used, they preferably have a diameter of from about 1 to about 2 mm and a length from about 3 to about 8 mm.

While the invention is not to be limited by theory, it is believed that arsine can react with the metallic nickel and/or with nickel oxide, forming arsenic metal, which either forms a NiAs alloy or is deposited on the support.

The absorbent material is usually prepared ex situ and stored either under a convenient saturated liquid hydrocarbon, like cyclohexane or dodecane or under a non-oxidizing atmosphere like $CO_2$ or $N_2$.

It has been found that propylene adsorbs onto the absorbent material when contacted with the feedstocks containing propylene during the arsine removal from said feedstocks, and that the propylene adsorption reaction is exothermic, occurring to a greater extent during start-up. Under certain conditions, and particularly when the absorbent material used is stored under a nonoxidizing atmosphere, the temperature rise may be very significant, more particularly at the surface of the material at which the temperature may be much higher than that measured with a thermocouple, and it may thus damage the absorbent material. In addition the high temperatures cause undesired side reactions, more particularly propylene dimerization and trimerization. The dimers are hexenes which copolymerize with propylene and break the regularity of the linear chain of isotactic polypropylene. As a result, the copolymer has a lower crystallinity than polypropylene, and thus a lower melting point; its mechanical resistance is also lower.

It has been found that an excessive increase in the temperature of the absorbent material can be avoided by previously conditioning the material by passing over said material an inert gas flow containing a minor amount of at least one light olefin, preferably propylene in a concentration of from about 0.1 to 5 vol %. The inert gas, which should be oxygen free (contain the least possible amount of oxygen), is usually nitrogen. It is preferable to begin the conditioning procedure by passing essentially pure inert gas. The conditioning step is preferably carried out at about atmospheric pressure and at or below ambient temperature. It is continued until the propylene concentration at the outlet equals that introduced. It is also possible to monitor the passage of an exotherm, shown by thermocouples introduced within the absorbent material.

It is known that, when the absorbent material is prepared ex situ and stored under a non-oxidizing atmosphere (usually stabilized under $CO_2$), the traces of oxygen usually present therein have a negative effect on the properties of the absorbent material. This negative effect can be prevented if the absorbent material is pretreated prior to its conditioning by passing therethrough, at a temperature of from about 150°-200° C. and preferably at about atmospheric pressure, a gaseous flow comprising first an inert gas (containing the least possible amount of oxygen) then a mixture of inert gas and hydrogen containing an increasing concentration of hydrogen, before purging it free of hydrogen with an inert gas flow.

In utilizing the latest generation of Ziegler-type catalysts in the production of polypropylene, it is of substantial importance that the propylene feedstock contains less than 50 ppb and preferably less than 30 ppb of arsine. It has been unexpectedly found that by passing the propylene feedstock over an absorbent material as herein before described, the feedstock obtained has an arsine content not exceeding 50 ppb. This result is unexpected due to the degree of purity obtained and due to the fact that this process can be carried out either in the presence or in the absence of water.

In polypropylene production, the hydrocarbon feedstock generally comprises more than 75 wt. % propylene, more particularly from about 85 to about 99 wt. % propylene, and up to about 10 ppm arsine. In one embodiment of the present invention, the propylene feedstock is passed over the absorbent material at a temperature of from about −10° C. to about 80° C., preferably of from about 10° C. to about 40° C., and under sufficient pressure to keep the medium in the liquid phase. The weight hourly space velocity (WHSV) utilized is from about 0.1 to about 25 kg/kg.h and preferably from about 1 to about 10 kg/kg.h.

In polyethylene production, the hydrocarbon feedstock generally comprises more than 80 wt. % of ethylene, more particularly from about 90 to about 99 wt. %, and up to about 10 ppm of arsine. Another embodiment of the present invention, the ethylene temperature of from about −10° C. to about 80° C., preferably from about 10° C. to about 40° C., under a pressure of at least 1 MPa (10 Bars), and with a WHSV of from about 0.1 to about 25 kg/kg.h, preferably of from about 1 to about 10 kg/kg.h.

The examples which follow are given in order to provide a better illustration of the process of the present invention, but without thereby restricting its scope.

EXAMPLE 1

A liquid hydrocarbon feedstock containing 99.5% of propylene, less than 5 ppm of water, and having a residual arsine content of 150,000 ppb was passed over an absorbent material consisting of 43.3% by weight of silica-alumina as the support, on which nickel was deposited, the nickel being present in the form of NiO and of metallic Ni, the weight ratio of metallic nickel to nickel oxide being of 0.668.

Before reduction, the absorbent material contained about 49% by weight nickel.

The absorbent material was finely divided to give an average particle size of about 1 mm. The specific surface area of this material was 145 m$^2$/g, while its bulk density was of 0.81. It was stored under cyclohexane.

The above-mentioned feedstock was passed in the upflow mode through the absorbent material at a temperature of 25° C., under a pressure of 1.5 MPa (15 bars) sufficient to keep the feedstock in the liquid phase and at a WHSV of 3.7 kg/kg.h.

The purified feedstock had an arsine content as shown in Table I. Assuming that all arsine was absorbed during the first 96 hours, the capacity of the absorbent may thus be calculated to be of at least 53 g arsine/kg absorbent.

TABLE I

| Hours | Arsine (ppb) |
| --- | --- |
| 24 | <50 |
| 48 | <50 |
| 72 | <50 |
| 96 | 100 |

EXAMPLE 2

A liquid hydrocarbon feedstock containing 99 wt. % propylene, 10 ppm of water and having a residual arsine content of 305 ppb was passed over the same absorbent material as in Example 1, at a temperature of 20° C., a pressure of 1.5 MPa (15 bars) sufficient to keep the feedstock in the liquid phase, and at a WHSV of 6 kg/kg.h. After 24 hours, the purified feedstock still had an arsine content lower than 3 ppb, even though the feed contained water.

A polymerization test was carried out, using a Ziegler-type catalyst. Under identical conditions, the yield, expressed as the weight ratio of polypropylene to catalyst, was of 10,000 for the unpurified feed and of 32,000 for the purified feedstock.

EXAMPLE 3

A liquid hydrocarbon feedstock containing 95.6 wt. % propylene, 3.8 wt. % propane and 0.6 wt. % C$_4$ hydrocarbons, the water content of which was about 30 ppm, and having a residual arsine content of 60 ppb was passed over the same absorbent as described in Example 1. This example is given to illustrate the activity of the absorbent over a long period of time.

The feedstock was passed under a pressure of 1.5 MPa (15 bars), at a temperature of 24° C., and with a WHSV of 6 kg/kg.h.

The arsine concentrations in the effluent are indicated in Table II.

TABLE II

| Day | Arsine (ppb) |
| --- | --- |
| 2 | <3 |
| 5 | 3 |
| 16 | <3 |

This example shows that even after 16 days the activity of the absorbent material remained very high, even though the feed contained water.

EXAMPLE 4

An absorbent material as described in Example 1 was prepared and stored under carbon dioxide for one month.

The absorbent material was pretreated by passing a gaseous flow thereon, at a temperature of 180° C. and under atmospheric pressure, said gaseous flow being formed first of nitrogen during 14 hours, then a mixture of nitrogen and hydrogen during a further 24 hours, the hydrogen concentration therein being increased by about 5 vol % per hour up to more than 95 vol %. The absorbent material was cooled under said flow of nitrogen and hydrogen, then purged free of hydrogen with a nitrogen flow.

The absorbent material was then conditioned. A nitrogen flow was passed during 4 hours over the absorbent material, under atmospheric pressure, at a temperature of 20° C., and with a gaseous hourly space velocity (GHSV) of 125 l/l.h. During a further 12 hour period, the conditioning was continued under the same conditions with nitrogen containing 1 vol % propylene.

The purification procedure of Example 1 was repeated with the conditioned material. Results similar to Example 1 were obtained and the purified feedstock had an arsine content as shown in Table III at the conclusion of the periods indicated.

TABLE III

| Time | Arsine concentration |
| --- | --- |
| 36 | <50 |
| 60 | <50 |
| 84 | <50 |
| 108 | 200 |

Having described specific embodiments of the present invention, it will be understood that modification thereof may be suggested to those skilled in the art, and it is intended to cover all such modifications as fall within the scope of the appended claims.

We claim:

1. A process for removing arsine from a light olefin-containing hydrocarbon feedstock, said process comprising the steps of:
    (a) passing said feedstock over an absorbent material comprising nickel deposited on a support material wherein said nickel is present as both nickel oxide and metallic nickel; and
    (b) recovering a hydrocarbon stream from said absorbent material having a substantially reduced arsine content.

2. The process of claim 1 wherein said nickel oxide and metallic nickel are present in an amount of up to about 80 wt. % of the absorbent material, and said metallic nickel is present in an amount within the range of 10 wt. %–50 wt. % of the absorbent material.

3. The process of claim 2 wherein the weight ratio of metallic nickel to nickel oxide is within the range of about 0.4–2.0, and the absorbent material comprises from about 30–60 wt. % of the support material.

4. The process of claim 1 wherein sad absorbent material has a specific surface area with the range of about 100–200 m²/g.

5. The process of claim 1 wherein the feedstock contains more than 75% by weight of propylene.

6. The process of claim 5 wherein said feedstock contains from about 85 to 99 wt. % of propylene.

7. The process of claim 5 wherein said feedstock is passed over said absorbent material at a temperature in the range of about $-10°$ C. to $80°$ C. under sufficient pressure to retain the feedstock in the liquid phase and at a WHSV in the range of about 0.1 to 25 kg/kg.h.

8. The process of claim 1 wherein the feedstock contains more than 80 wt. % of ethylene.

9. The process of claim 8 wherein the feedstock contains from about 90 to 99 wt. % ethylene.

10. The process of claim 8 wherein said feedstock is passed over said absorbent material at a temperature range of about to $-10°$ C. to $80°$ C. under a pressure in the of at least 1 MPa and at a WHSV in the range of about 0.1 to 25 kg/kg.h.

11. The process of claim 7 wherein said feedstock is passed over said absorbent material at a temperature in the range of about $10°$ C. to $40°$ C. and at a WHSV, in the range of about 1 to 10 kg/kg/h.

12. The process of claim 10 wherein said feedstock is passed over said absorbent material at a temperature in the range of about $10°$ C. to $40°$ C. and at a WHSV, in the range of about 1 to 10 kg/kg/h.

13. The process of claim 1 further comprising the step of, prior to step (a), conditioning the absorbent material by passing a flow of inert gas containing a minor amount of at least one light olefin over said absorbent material.

14. The process of claim 13 wherein said light olefin in said inert gas is propylene in a concentration in the range of about 0.1 to 5 vol. %.

15. The process of claim 13 further comprising the step of pretreating said absorbent material prior to said conditioning thereof by flowing initially an inert gas and thereafter a mixture of an inert gas and hydrogen over said absorbent material at a temperature within the range of $150°$ to $250°$ C. and progressively increasing the concentration of hydrogen in said mixture of inert gas and hydrogen.

16. The process of claim 15 wherein said inert gas and said mixture of inert gas and hydrogen are passed over said absorbent material at about atmospheric pressure.

17. The process of claim 15 further comprising the step of subsequent to flowing said mixture of inert gas and hydrogen over said absorbent material, flowing an inert gas over said absorbent material to purge hydrogen from said absorbent material.

18. The process of claim 1 wherein the recovered stream has an arsine concentration not exceeding 50 parts per billion by weight.

19. The process of claims 18 wherein the arsine original concentration in the feed is of no more than about 70 parts per million by weight.

20. A process for removing arsine from a hydrocarbon feedstock employing an absorbent material for arsine which reacts exothermically in adsorption of a hydrocarbon component of said feedstock comprising the steps of:
(a) passing an inert gas containing a minor amount of said hydrocarbon component over the absorbent material in order to condition the absorbent material to alleviate an excess temperature increase during the processing of said hydrocarbon feedstock,
(b) thereafter passing said hydrocarbon feedstock containing said hydrocarbon component in a concentration substantially greater than the concentration of said hydrocarbon component in the inert gas over the conditioned absorbent material to selectively absorb arsine on said absorbent material, and
(c) recovering a hydrocarbon stream containing said hydrocarbon component and having a substantially reduced arsine concentration from said absorbent material.

21. The process of claim 20 wherein said hydrocarbon component comprises an olefinic hydrocarbon.

22. The process of claim 21 wherein said olefinic hydrocarbon is propylene.

23. The process of claim 22 wherein said propylene is present in said inert gas in a concentration within the range of 0.1 to 5 vol. %.

24. The process of claim 23 wherein said hydrocarbon feedstock contains propylene in a concentration of more than 75 wt. %.

25. The method of claim 20 wherein said inert gas containing a minor amount of said hydrocarbon component is passed over said absorbent material until the concentration of said hydrocarbon component in the effluent from said absorbent material equals the concentration of said hydrocarbon component in the inert gas introduced to the absorbent material and thereafter passing said hydrocarbon feedstock containing arsine over said absorbent material.

* * * * *

UNITED STATES PATENT AND TRADEMARK OFFICE
CERTIFICATE OF CORRECTION

PATENT NO. : 4,861,939

DATED : August 29, 1989

INVENTOR(S) : Debras et al

It is certified that error appears in the above-identified patent and that said Letters Patent is hereby corrected as shown below:

| | | |
|---|---|---|
| Col. 2, Line 42 | – | Change "5b H3" to "Sb $H_3$" |
| Col. 3, Line 18 | – | Add "are" after "methods" |
| Col. 7, Line 28 | – | Delete "to" after "about" |
| Col. 7, Line 33 | – | Delete "," after "WHSV" |
| Col. 7, Line 34 | – | Change "Kg/Kg/h " to "Kg/Kg.h" |
| Col. 7, Line 37 | – | Delete "," after "WHSV" |
| Col. 7, Line 38 | – | Change "Kg/Kg/h " to "Kg/Kg.h" |

Signed and Sealed this

Twenty-eighth Day of May, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,861,939

DATED : August 29, 1989

INVENTOR(S) : Guy Debras
Philippe Bodart

It is certified that error appears in the above-identified patent and that said Letters Patent is hereby corrected as shown below:

Col. 3, Line 29 — Add "(" before "nm)"

Col. 7, Line 10 — Change, "sad" to "said"

Col. 7, Line 28 — After "temperature" insert --in the --

Col. 7, Line 29-30 — Delete "in the"

Signed and Sealed this

Tenth Day of December, 1991

Attest:

HARRY F. MANBECK, JR.

*Attesting Officer*  *Commissioner of Patents and Trademarks*